United States Patent [19]

Gaffar et al.

[11] Patent Number: 4,474,750

[45] Date of Patent: Oct. 2, 1984

[54] ANTICALCULUS ORAL COMPOSITION

[75] Inventors: Abdul Gaffar, Somerset; John F. Gerecht, Bridgewater, both of N.J.

[73] Assignee: Colgate-Palmolive Company, New York, N.Y.

[21] Appl. No.: 469,374

[22] Filed: Feb. 24, 1983

[51] Int. Cl.³ .......................... A61K 7/16; A61K 7/24
[52] U.S. Cl. .......................................... 424/49; 424/55
[58] Field of Search ...................................... 424/49–58

[56] References Cited

U.S. PATENT DOCUMENTS 4,080,441  3/1978  Gaffar et al. .......................... 424/54

*Primary Examiner*—Shep K. Rose
*Attorney, Agent, or Firm*—Herbert S. Sylvester; Murray M. Grill; Robert L. Stone

[57] ABSTRACT

A substantially anhydrous oral composition is disclosed which is substantially devoid of normally staining antibacterial antiplaque agents and which contains an effective anticalculus amount of a bis(o-carboxyphenyl) ester of a $C_{2-8}$ aliphatic dicarboxylic acid such as bis(o-carboxyphenyl) succinate.

4 Claims, No Drawings

ANTICALCULUS ORAL COMPOSITION

This is a continuation of application Ser. No. 317,803 filed Nov. 3, 1981 now abandoned.

This application is related to U.S. Pat. No. 4,080,441, the entire disclosure of which is incorporated herein by reference.

This invention relates to oral compositions containing an anticalculus agent.

Calculus is a hard, mineralized formation which forms on the teeth. Regular brushing prevents a rapid build-up of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline hydroxyapatite is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including hydroxyapatite. A suggested mechanism by which the nontoxic anticalculus agents of this invention inhibit calculus formation probably involves such agents functioning to bind the amino groups in the matrix system in the oral cavity at physiological pH and temperatures and also cross-links the protein.

A substantial number of different types of compounds and compositions have been developed for use as antibacterial, and antiplaque and anticalculus agents in oral compositions, including for example such cationic materials as the bis-biguanide compounds and quaternary ammonium compounds, e.g. benzethonium chloride and cetyl pyridinium chloride, disclosed in U.S. Pat. No. 4,080,441. These cationic materials however tend to stain the teeth with continued use.

It is an object of this invention to provide an improved anticalculus oral composition which will have relatively little or no tendency to stain the teeth.

A further object of the invention is to provide an oral composition which inhibits the transformation of amorphous calcium phosphate to hydroxyapatite crystal structure normally associated with calculus.

Another object of this invention is the provision of an improved method for inhibiting the formation of calculus.

Other objects and advantages will appear as the description proceeds.

In accordance with certain of its aspects, this invention relates to a substantially anhydrous oral composition substantially devoid of stain-inducing antibacterial antiplaque agents and comprising an orally acceptable vehicle and in an effective amount as an anticalculus agent at least one bis(o-carboxy phenyl) ester of a $C_{2-8}$ aliphatic dicarboxylic acid, and the application of such composition to the teeth.

The anticalculus agents of this invention may be represented, in their free acid form, by the formula:

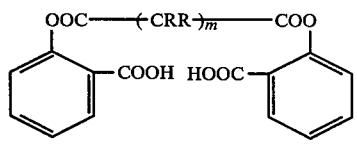

wherein preferably the R's are independently H or $C_{1-4}$ alkyl, preferably H, and n is an integer of 0 to 6, preferably 2, the preferred anticalculus agent accordingly being bis(o-carboxyphenyl) succinate (BOCS). The $-(CRR)_n-$ group may however be a single bond when n is 0 as in the bisesters of oxalic acid, or may be any $C_{1-6}$ alkylene or alkenylene group, i.e. straight or branched saturated or unsaturated, O or S chain interrupted, $C_{1-4}$ alkoxy substituted, or the like. When the —CRR group is part of an ethylenic group, one or both R's may be zero, i.e. replaced by a valence bond. The bis(o-carboxyphenyl) esters of the following aliphatic dicarboxylic acids are only illustrated of the anticalculus agents of this invention:

oxalic (ethanedioic)
malonic (propanedioic)
succinic (butanedioic)
glutaric (pentanedioic)
adipic (hexanedioic)
pimelic (heptanedioic)
suberic (octanedioic)
maleic (1,2-ethylenedicarboxylic HOOCCH:CH—COOH)
itaconic (methylenesuccinic HOOCC(:CH$_2$)CH$_2$—COOH)
isosuccinic (2-methylpropanedioic)
muconic (2,4-hexadienedioic HOOCCH:CHCH:CH—COOH)
dihydromuconic (HOOCCH$_2$CH$_2$CH:CHCOOH)
dihydroitaconic (methylsuccinic)
3-ethylhexanedioic Further, one or both phenyl moieties in this agent may be nuclearly substituted with one or more $C_{1-4}$ alkyl or alkoxy groups such as methyl or isobutoxy, or halo such as chloro, bromo, iodo or fluoro.

Suitable methods for preparing these anticalculus agents are disclosed in the aforementioned U.S. Pat. No. 4,080,441. Another improved method for such preparation is described in Example A below.

It will be understood that the free acid form of these anticalculus agents may be converted to and employed in their equivalent salt form by treatment with any base containing an orally acceptable cation such as alkali metal (e.g. sodium, potassium), alkaline earth metal (e.g. calcium, magnesium), metal, ammonium, mono- di- or tri-$C_{1-18}$ alkyl or alkanol-substituted ammonium or organic amine (e.g. methyl, ethyl, hydroxyethyl substituents).

The anticalculus agents of this invention are antinucleating agents, oral compositions of this invention containing them are effective in reducing formation of dental calculus without unduly decalcifying the dental enamel, and in contrast to the above-mentioned cationic antibacterial, antiplaque and anticalculus agents, such agents and compositions have little or no tendency to stain the teeth, and can further be found to effectively reduce or inhibit gingivitis.

The concentration of these anticalculus agents in oral compositions can range widely, typically upward from about 0.01% by weight, with no upper limit on the amount that can be utilized except as dictated by cost or incompatibility with the vehicle. Generally, concentrations from about 0.01% to about 10%, preferably about 0.05% to about 8.0%, and more preferably about 0.1% to about 4% by weight are utilized. Oral compositions which in the ordinary course of usage could be accidentally ingested preferably contain concentrations in the lower portions of the foregoing ranges.

Although these anticalculus agents vary in water solubility depending upon their molecular weight, identity and proportions of salt-forming cations, etc, they are sufficiently soluble in aqueous media, e.g. in the oral cavity, in the low concentrations employed herein to be termed water soluble to that extent. It has however been unexpectedly found that oral compositions containing such agents in an aqueous medium undergo significant hydrolysis or other deterioration in storage. In accordance with a further aspect of this invention, it is preferred to provide oral compositions which are substantially anhydrous, e.g. containing 0 to less than about 0.2 moles of water per mole of the anticalculus agent.

When the oral compositions of this invention are in liquid, paste or cream form, as in mouthwashes and rinses, toothpastes and dental creams, a water-miscible (preferably water soluble) organic normally liquid orally acceptable vehicle is preferably employed. Typically, such vehicles include water soluble $C_{2-4}$ monohydric and polyhydric alkanes and $C_{1-4}$ alkyl ethers thereof such as ethanol, ethylene glycol, methyl, ethyl and butyl ethers thereof (methyl, ethyl and butyl Cellosolve), propylene glycol, tetramethylene glycol, and glycerin, and water soluble poly (ethylene glycols) such as diethylene glycol, methyl, ethyl, diethyl and butyl ethers thereof (methyl, ethyl, diethyl and butyl Carbitol), triethylene glycol, low molecular weight polyethylene glycols, e.g. 400, 600, and mixtures thereof etc. Polyhydric compounds in the aforementioned group, especially propylene glycol, glycerin, and the low molecular weight polyethylene glycols, generally function also as humectants which are desirable components of the oral compositions of this invention.

Other types of such water miscible liquid vehicles which may be employed are the polar aprotic solvents such as dimethyl formamide and sulfoxide, N-methyl pyrrolidone, sulfolane, tetramethyl sulfone, acetonitrile, and preferably ethylene and propylene carbonate.

Essentially water-immiscible organic liquid vehicles may also be employed representative of which are hydrocarbon, fatty acid and fatty acid ester oils such as mineral oil, tetradecane, pentane, caproic, acid, oenanthylic acid, methyl caproate and laurate, ethylene glycol dicaprylate and the like.

Mixtures of the same types and/or of different types of liquid vehicles as described above may of course be employed.

The proportion of the aforementioned liquid vehicle employed in these oral compositions will obviously depend for the most part upon the desired degree of fluidity or viscosity and will be readily determinable in routine manner in any particular instance. Typically, liquid compositions such as mouthwashes and rinses contain about 70% to about 99.9%, and toothpastes and dental creams contain about 10% to about 80%, by weight of such liquid vehicle, about 10% to about 100% of which may be a humectant. Normally solid humectants such as sorbitol may also be included.

The oral compositions of this invention typically have, in aqueous medium, e.g. in the oral cavity or in the form of a 20% aqueous slurry or solution, a pH of about 3.5 to about 8, preferably about 4 to about 7, more preferably about 4 to 6. Such pH can be controlled by inclusion of the required amounts of acidic substances such as citric or benzoic acid, basic substances such as sodium hydroxide, and/or buffering agents such as sodium citrate, benzoate, bicarbonate or carbonate, disodium hydrogen phosphate, sodium dihydrogen phosphate, or mixtures thereof.

The vehicle in solid or pasty compositions such as toothpowders, tablets, toothpastes and dental creams generally contains polishing material. Examples of polishing materials are water-insoluble sodium metaphosphate (IMP), potassium metaphosphate, tricalcium phosphate, anhydrous, monohydrated and dihydrated calcium and dicalcium phosphate, calcium pyrophosphate, magnesium orthophosphate, trimagnesium phosphate, magnesium and calcium carbonate and sulfate, alumina, hydrated alumina, aluminum silicate, alkali metal and alkaline earth metal aluminosilicates, zirconium silicate, silica, bentonite, and mixtures thereof. Preferred polishing materials include crystalline and colloidal silica, silica gel, complex amorphous alkali metal aluminosilicate, hydrated alumina and IMP.

Alumina, particularly the hydrated alumina sold by Alcoa as C333, which has an alumina content of 64.9% by weight, a silica content of 0.008%, a ferric oxide content of 0.003%; and a moisture content of 0.37%, at 110° C., and which has a specific gravity of 2.42 and a particle size such that 100% of the particles are less than 50 microns and 84% of the particles are less than 20 microns, is very effective.

When visually clear gels are employed, a polishing agent of colloidal silica, such as those sold under the trademark SYLOID as Syloid 72, 74 or 244 or under the trademark SANTOCEL as Santocel 100 and alkali metal aluminosilicate complexes are particularly useful, since they have refractive indices close to the refractive indices of gelling agent-liquid systems commonly used in dentifrices.

Many of the so-called "water-insoluble" polishing material are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than about 37 microns.

The polishing material is generally present in amounts ranging from about 20% to about 99% by weight of the oral preparation. Preferably, it is present in amounts ranging from 20% to about 75% in toothpaste, and from about 70% to about 99% in toothpowder.

In the preparation of toothpowders, it is usually sufficient to admix mechanically, e.g., by milling, the various solid ingredients in appropriate quantities and particle sizes.

In a toothpaste, cream or gel, the liquids and solids typically are suitably proportioned to form a creamy or gelled mass which is extrudable from a pressurized container or from a collapsible tube. Thickening to the proper desired viscosity or flowability is typically facilitated or achieved by inclusion of a binding, thickening or gelling agent such as natural or synthetic gums or gum-like materials, typically Irish moss, Pluronics, sodium carboxymethylcellulose and carboxyethylcellulose, methylcellulose, hydroxyethyl cellulose, hydroxypropyl cellulose, hydroxypropyl methylcellulose, hydroxybutyl methylcellulose, Laponite CP or SP (synthetic hectorite clay of Laporte Industries Ltd.), viscarin, gelatin, glucose, sucrose, Carbopois (e.g. 934,940,941), gum karaya, gum arabic, gum tragacanth, polyvinylpyrrolidone, polyvinyl alcohol and starch. They are usually present, singly or plurally, in an amount up to about 10% by weight, preferably in the range of from about 0.5% to about 5%. The preferred gelling agents are Pluronics and hydroxypropyl cellulose. Pluronics such as F108 and F127 are polyoxypropylene polyoxyethylene block polymers which simultaneously function as nonionic surfactants.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31–38 and such suitable nonionic surfactants in col. 8, lines 30–68 and col. 9, lines 1–12, which passages are incorporated herein by reference thereto.

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, calcium fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be nontoxic amount. In a thickened or solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005% to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount up to 7.6% by weight, more typically about 0.5 to about 1% by weight.

In a liquid oral preparation such as a mouthwash, the fluorine-providing compound is typically present in an amount sufficient to release up to about 0.0005 to about 0.2%, preferably about 0.001 to about 0.1% and more preferably about 0.0013% by weight of fluoride ion.

Various other materials may be incorporated in the oral preparations of this invention such as whitening agents, preservatives, silicones, chlorophyll compounds, other anticalculus agents, antibacterial antiplaque agents, and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed.

Examples of suitable flavoring constituents are flavoring oils, e.g., oils of spearmint, peppermint, wintergreen, sassafras, clove, sage, eucalyptus, marjoram, cinnamon, lemon, and orange, menthol, eugenol, cineol, and methyl salicylate. Suitable sweetening agents include sucrose, fructose, lactose, maltose, sorbitol, xylitol, sodium cyclamate, perillartine, APM (aspartyl phenyl alanine, methyl ester) and saccharine. Suitably, flavor and sweetening agents may together comprise from about 0.01% to 5% or more of the preparation.

In preparing the oral compositions of this invention, it is preferred but not essential to add the anticalculus agent after the other ingredients (except perhaps some of the water) are mixed or contacted with each other to avoid a tendency for such agent to be precipitated.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum, lined lead or plastic, or other squeeze dispenser for metering out the contents, having a label describing it, in substance, as a toothpaste or dental cream.

In the practice of this invention an oral composition according to this invention such as a mouthwash or toothpaste containing the described anticalculus agent in an amount effective to inhibit calculus on dental surfaces is applied regularly to the oral cavity, especially dental enamel, preferably from about 1 to 3 times daily.

EXAMPLE A

Preparation of Bis(o-carboxyphenyl)succinate 0.4 moles salicylic acid (55.2 grams)
0.4 moles pyridine (31.2 ml.)
0.2 moles succinyl chloride (31.0 grams)

The salicylic acid and pyridine are dissolved in 90 ml. of acetone. To the resulting clear solution, the succinyl chloride in 90 ml. of acetone is added, with stirring, at a rate to keep acetone refluxing for half an hour. During this addition, the desired BOCS product begins to separate and the mixture turns dark purple. The reaction slurry is stirred for half an hour after all the succinyl chloride has been added. Then 200 ml. of water are added, the acetone evaporated from the slurry in a rotary evaporator at 35° C. and the desired BOCS product collected on a suction filter, washed with water and dried in vacuum at 60° C.

Yield—66.5 grams (93%).
M.P. 177°–177.5° C.
Neutral.Equivalent 179.9.
Saponification Eq. 186.8.
Calculated for $C_{18}H_{14}O_8$.

The following examples are further illustrative of the nature of the present invention, but it is understood that the invention is not limited thereto. All amounts and proportions referred to herein and in the appended claims are by weight, and temperatures are in °C., unless otherwise indicated.

EXAMPLE 1

The following formulation is illustrative of a toothpaste in accordance with this invention effective for inhibiting calculus.

|  | Parts by Weight |
|---|---|
| Propylene | 42.0 |
| Hydroxypropyl cellulose | 1.0 |
| Polyethylene glycol 600 | 10.0 |
| Sodium saccharin | 0.2 |
| $TiO_2$ | 0.4 |
| IMP | 28.0 |
| Syloid 244 | 12.0 |
| Sodium lauryl sulfate | 1.5 |
| Flavor | 1.0 |
| BOCS | 3.0 |

The following formulations, given in parts by weight, are illustrative of mouthwashes in accordance with this invention effective for inhibiting calculus.

|  | Example | | |
|---|---|---|---|
|  | 2 | 3 | 4 |
| Flavor | 0.22 | 0.22 | 0.22 |
| Ethanol | 15.0 | 15.0 | 15.0 |
| Pluronic F108 | 3.0 | 3.0 | 3.0 |
| Glycerine | 10.0 | 10.0 | 10.0 |
| Sodium saccharin | 0.03 | 0.03 | 0.03 |
| BOCS | 0.05 | 0.50 | 1.0 |

The mouthwash formulations of Examples 2–4 above may be applied to the oral cavity as is or after dilution with about 2 to 4 times their volumes of water, i.e. volume ratios of formulation: water of about 1:2 to about 1:4.

Substitution of equivalent amounts of the following bis ester-containing compounds for the BOCS employed in the formulations of Examples 2–5 yield formulations also effective for inhibiting dental calculus.

| Example | Bis Ester-Containing Compound |
|---|---|
| 5 | bis(2-carboxy-4-butoxyphenyl)oxalate |
| 6 | bis(2-carboxy-4-propyl-6-chlorophenyl)glutarate |

-continued

| Example | Bis Ester-Containing Compound |
|---|---|
| 7 | bis(2-carboxy-4-methyl-6-bromophenyl)adipate |
| 8 | bis(2-carboxy-4-iodo-6-ethoxyphenyl)suberate |
| 9 | bis(2-carboxyphenyl)pimelate |
| 10 | bis(2-carboxy-5-methoxyphenyl)malonate |
| 11 | bis(2-carboxy-6-butylphenyl)maleate |
| 12 | bis(2-carboxyphenyl)itaconate |
| 13 | bis(2-carboxy-4-fluorophenyl)muconate |

EXAMPLE 14

In this study on 24 rats, a placebo of water and an 0.1% solution of BOCS in dimethyl sulfoxide, pH 7.10, as the test anticalculus mouthrinse are evaluated for effectiveness against formation of calculus for a 30 day period. Litter matured Osborne-Mendel rats are used. On days 21 and 22 they are inoculated intraorally with Strep-mutans and Actinomyces viscsous and feces from caries-active Osborne-Mendel rats, placed on calculogenic diet 580F supplemented with 0.2% P as $Na_2pO_4$, and the placebo and the test mouthrinse each applied to molars of a group of 12 such rats twice daily on Monday to Friday and once daily on Saturday and Sunday for a period of 30 days. The animals are weighed at the beginning and at the end of the study to assure that the rats remain in otherwise normal condition. At the end of the period, calculus formation is assessed according to routine procedures and the following results are found:

|  | No. Animals | Mean Terminal Weight Gain | Mean Calculus Units* | Significance |
|---|---|---|---|---|
| Placebo (Water) | 12 | 128 grams | 17.9 |  |
| Mouthrinse (0.1% BOCS) | 12 | 135 grams | 14.8 | $\alpha < 0.01$ |

*20 units at risk

The above results establish that BOCS at 0.1% level when applied topically is significantly effective (at the ±99% level) in reducing calculus formation.

This invention has been described with respect to preferred embodiments and it will be understood that modifications and variations thereof obvious to those skilled in the art are to be included within the spirit and purview of this application and the scope of the appended claims.

What is claimed is:

1. A method of inhibiting oral calculus comprising applying to the oral cavity a calculus-inhibiting amount of a substantially anhydrous oral composition devoid of stain inducing antibacterial antiplaque agents and consisting essentially of an orally acceptable vehicle and in an effective amount as an anticalculus agent at least one bis (O-carboxyphenyl) ester of $C_{2-8}$ aliphatic dicarboxylic acid.

2. The method of claim 1 wherein said anticalculus agent is bis (O-carboxyphenyl) succinate.

3. The method of claim 2 wherein said composition is a toothpaste also containing a liquid vehicle, a gelling agent and a dentally acceptable polishing agent and having, in aqueous medium, a pH of about 3.5 to about 8.

4. The method of claim 2 wherein said composition is a mouthwash containing a liquid vehicle and having, in aqueous medium a pH of about 3.5 to about 8.

* * * * *